United States Patent [19]

Gray

[11] Patent Number: 5,510,352
[45] Date of Patent: Apr. 23, 1996

[54] METHODS OF USING (+) DOXAZOSIN FOR THE TREATMENT OF HYPERTENSION

[75] Inventor: Nancy M. Gray, Marlboro, Mass.

[73] Assignee: Sepracor, Inc., Marlborough, Mass.

[21] Appl. No.: 207,802

[22] Filed: Mar. 7, 1994

Related U.S. Application Data

[63] Continuation of Ser. No. 970,677, Nov. 4, 1992, abandoned.
[51] Int. Cl.⁶ .................................................. A61K 31/495
[52] U.S. Cl. ............................................................. 514/254
[58] Field of Search ............................................. 514/254

[56] References Cited

U.S. PATENT DOCUMENTS

| | | | |
|---|---|---|---|
| 4,188,390 | 2/1980 | Campbell | 424/251 |
| 5,114,714 | 5/1992 | Young et al. | 424/400 |
| 5,114,715 | 5/1992 | Young et al. | 424/400 |
| 5,212,176 | 5/1993 | Kyncl et al. | 514/254 |

OTHER PUBLICATIONS

"Doxazosin—A Review of Its Pharmacodynamic and Pharmacokinetic . . ." Young et al. *Drug Evaluation 35* 525–541 (1988).
"Optimisation of Chiral Separation of Doxazosin Enantiomers by High-Performance Liquid Chromatography on a Second Generation $\alpha_1$-Acid Glycoprotein Column" Ley et al. *Recent Advances in Chiral Separations* 97–103 (1991).
"A Pharmacodynamic and Pharmacokinetic Assessment of a New $\alpha$-Adrenoceptor Antagonist, Doxazosin (UK33274) In Normotensive Subjects" Elliott et al. *Br. J. Clin. Pharmac.* 13 699–703 (1982).
"Scrip's New Product Review No. 12 Doxazosin" No Author *PJB Publications Ltd.* 1–17 (1986).
"Mechanisms Contributing to the Arrhythmogenic Influences of Alpha-Adrenergic Stimulation in the Ischemic Heart" Corr et al., *Am. J. of Med.* 87 19S–25S (1989).
"2,4–Diamino–6,7-dimethoxyquinazolines. 1. 2-[4-(1, 4-Benzodioxan-2-ylcarbonyl)piperazin-1-yl] Derivatives as $\alpha_1$-Adrenoceptor Antagonists and Antihypertensive Agents" Campbell et al. *J. Med. Chem.* 30, 49–57 (1987).
"Stereoselectivity in pharmacodynamics and pharmacokinetics" Ariëns *Schweiz. Med. Wochenschr.* 120, 131–134 (1990).
"Racemische therapeutica probleemmiddelen" Ariëns *Pharm. Weekblad* 125(22) 552–554 (1990).
"Racemates Versus Enantiomers in Drug Development": Dogmatism or Pragmatism? Testa et al. *Chirality* 2 129–133 (1990).
"Racemic therapeutics—ethical and regulatory aspects" Ariëns *Eur. J. Clin. Pharmacol.* 41 89–93 (1991).

Primary Examiner—Marianne M. Cintins
Assistant Examiner—William R. A. Jarvis
Attorney, Agent, or Firm—Heslin & Rothenberg

[57] ABSTRACT

Methods are disclosed utilizing the optically pure (+) isomer of doxazosin. This compound is a potent drug for the treatment of hypertension while avoiding the concomitant liability of adverse effects associated with the racemic mixture of doxazosin.

8 Claims, No Drawings

METHODS OF USING (+) DOXAZOSIN FOR THE TREATMENT OF HYPERTENSION

This application is a continuation of application Ser. No. 07/970,677, filed Nov. 4, 1992, now abandoned.

BACKGROUND OF THE INVENTION

This invention relates to novel compositions of matter containing optically pure (+) doxazosin. These compositions possess potent long lasting anti-hypertensive activity while avoiding adverse effects associated with the administration of the racemic mixture of doxazosin including but not limited to orthostatic hypotension, nausea, lethargy, fatigue and dizziness. Also disclosed are methods for treating hypertension in a human while avoiding adverse effects that are associated with the racemic mixture of doxazosin by administering the (+) isomer of doxazosin to said human.

The active compound of these compositions and methods is an optical isomer of doxazosin, which is described by Young and Brogden in *Drugs*, 35, 525–541 (1988) and U.S. Pat. No. 4,188,390. Chemically, the active compound is the (+) isomer of 4-amino-2-[4-(1,4-benzodioxan-2-carbonyl)piperazin-1-yl]-6,7-dimethoxyquinazoline also known as 1-(4-amino-6,7-dimethoxy-2-quinazolinyl)-4-[( 2,3-dihydro1,4-benzodioxan-2-yl)carbonyl]piperazine hereinafter referred to as doxazosin.

(+) Doxazosin, which is the subject of the present invention, is available commercially only as the 1:1 racemic mixture. That is, (+) doxazosin is available only as a mixture of optical isomers, called enantiomers. The racemic mixture of doxazosin is commercially available for administration as a methanesulfonate (mesylate) salt, but extensive pharmacology has been published on the hydrochloride salt as well.

Many organic compounds exist in optically active forms, i.e. they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. There is no correlation between nomenclature for the absolute stereochemistry and for the rotation of an enantiomer. Thus, D-lactic acid is the same as (−) lactic acid, and L-lactic acid is (+). For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Doxazosin is a representative of a group of drugs that block $\alpha_1$ adrenoceptors. $\alpha_1$ Receptors are innervated by postganglionic sympathetic neuronal fibers and are located in many body systems, including the cardiovascular system, where they are found primarily on smooth muscle cells in arterioles and venous capacitance vessels. Activation of these receptors by the physiological neurotransmitter substance, norepinephrine, increases peripheral arteriolar resistance and decreases venous capacitance. Specific $\alpha_1$ antagonists act to lower blood pressure and this is their primary current clinical indication.

Historically, $\alpha_1$ antagonists such as phenoxybenzamine and phentolamine were not particularly useful as antihypertensive agents largely because of the substantial tachycardia which accompanied their use. The tachycardic effect was however due primarily to the concomitant presynaptic $\alpha_2$ receptor blocking activity of the early $\alpha$ antagonists. Inhibition of $\alpha_2$ receptors acts presynaptically to augment the release of norepinephrine from adrenergic neurons. This stimulated the post-junctional sympathetic adrenoceptors in the heart which are predominately of the $\beta$ adrenergic type. New, more specific, $\alpha_1$ receptor antagonists produce much less tachycardia than the older compounds. During long term therapy the vasodilation persists with the newer $\alpha_1$ antagonists, but the remaining tachycardia, renin release and increased cardiac output, which are all reflex mediated, return to normal. In addition, there may be a component to $\alpha_1$ receptor inhibition that contributes to the amelioration of the reflex mediated mechanisms.

A troublesome cardiovascular problem related to the use of $\alpha_1$ receptor antagonists is orthostatic hypotension. Symptomatic orthostatic hypotension is most likely to occur with high initial doses of $\alpha_1$ antagonists or may occur when the dose is increased rapidly. A modest degree of fluid retention which is another result of vasodilation may also be observed when $\alpha_1$ antagonists are used as single agents.

Doxazosin is a selective $\alpha_1$ adrenergic receptor blocking agent structurally related to prazosin. Its oral bioavailability is good and the plasma half life in man is approximately 10 hours following both oral and intravenous administration.

Doxazosin has a single chiral center located on the carbon adjacent to the carboxyl group. This gives rise to a pair of enantiomers which have been resolved by Ley et al. [*Recent Advances in Chiral Separations*, Steven and Wilson Editors, Plenum Press, New York (1991) pages 97–103] on an analytical scale (0.52 µg), but there are no reports in the literature of a preparative-scale separation of the enantiomers.

The racemic mixture of doxazosin is presently used primarily as an antihypertensive agent. In addition, there is a report that the administration of doxazosin leads to modestly decreased total cholesterol and LDL levels.

Many of the $\alpha_1$ antagonists cause somewhat similar adverse effects. The incidence of reported side effects associated with racemic doxazosin-treated patients has varied among studies. The incidence of total side effects associated with doxazosin in patients treated for hypertension has ranged between 0 and 75%, but has generally been similar to that seen with other anti-hypertensive agents at dosages producing a similar reduction in blood pressure. The most frequently reported side effects have been postural hypotension, nausea, lethargy, fatigue and dizziness.

Thus it would be particularly desirable to find a compound with the advantages of the racemic mixture of doxazosin which would not have the aforementioned disadvantages.

SUMMARY OF THE INVENTION

It has now been discovered that the optically pure (+) isomer of doxazosin is an effective antihypertensive that avoids adverse effects associated with the administration of the racemic mixture, including but not limited to postural hypotension, nausea, lethargy, fatigue and dizziness. The present invention also includes methods for treating hypertension in a human while avoiding the adverse effects that are associated with the racemic mixture of doxazosin, by administering the optically pure (+) isomer of doxazosin to said human.

DETAILED DESCRIPTION OF THE INVENTION

The present invention encompasses a method of treating hypertension in a human, which comprises administering to a human in need of such antihypertensive therapy, an amount of (+) doxazosin, or a pharmaceutically acceptable salt thereof, substantially free of its (−) stereoisomer, said amount being sufficient to alleviate hypertension. The method avoids the concomitant liability of adverse effects associated with the administration of racemic doxazosin by providing an amount of (+) doxazosin which is insufficient to cause the adverse effects associated with the racemic mixture of doxazosin.

The present invention also encompasses an antihypertensive composition for the treatment of a human in need of antihypertensive therapy, which comprises an amount of (+) doxazosin, or a pharmaceutically acceptable salt thereof, substantially free of its (−) stereoisomer, said amount being sufficient to alleviate said hypertension but insufficient to cause the adverse effects associated with racemic doxazosin.

The available racemic mixture of doxazosin (i.e. a 1:1 racemic mixture of the two enantiomers) possesses antihypertensive activity and provides therapy and a reduction of symptoms in conditions and disorders related to hypertension; however, this racemic mixture, while offering the expectation of efficacy, causes adverse effects. Utilizing the substantially optically pure or optically pure isomer of doxazosin results in clearer dose related definitions of efficacy, diminished adverse effects, and accordingly, an improved therapeutic index. It is therefore more desirable to administer the (+) isomer of doxazosin than racemic doxazosin.

The term "adverse effects" includes, but is not limited to postural hypotension, nausea, lethargy, fatigue and dizziness. Other side effects that have been reported with doxazosin include headache, blurred vision, edema, chest discomfort, constipation, dry mouth, sexual dysfunction, anxiety or nervousness, insomnia, palpitations, tachycardia, rash, paresthesia, muscle cramps, increased sweating, conjunctivitis, diarrhea, flatulence, dyspnea, neutropenia, leukopenia, rhinitis and increased frequency of micturition.

The term "substantially free of its (−) stereoisomer" as used herein means that the compositions contain a greater proportion of the (+) isomer of doxazosin in relation to the (−) isomer. In a preferred embodiment, the term "substantially free of its (−) isomer" as used herein means that the composition is at least 90% by weight of (+) doxazosin and 10% by weight or less of (−) doxazosin. In a more preferred embodiment the term "substantially free of the (−) stereoisomer" means that the composition contains at least 99% by weight of (+) doxazosin, and 1% or less of (−) doxazosin. In the most preferred embodiment, the term "substantially free of its (−) stereoisomer" as used herein means that the composition contains greater than 99% by weight of (+) doxazosin. These percentages are based upon the total amount of doxazosin in the composition. The terms "substantially optically pure (+) isomer of doxazosin" or "substantially optically pure (+) doxazosin" and "optically pure (+) isomer of doxazosin" and "optically pure (+) doxazosin" are also encompassed by the above-described amounts.

The chemical synthesis of the racemic mixture of doxazosin can be performed by the method described in U.S. Pat. No. 4,188,390. The individual enantiomers of doxazosin may be obtained by resolution of the racemic mixture of enantiomers using conventional means. The doxazosin may be resolved with an optically active acid such as tartaric acid at the N-(1,4-benzodioxan-2-carbonyl)piperazine intermediate stage or at the final product. Alternatively the benzodioxancarboxylic acid intermediate can be resolved with an optically active base such as brucine or α-phenethylamine. Other standard methods of resolution known to those skilled in the art, including but not limited to simple crystallization and chromatographic resolution, can be used. [See for example, Stereochemistry of Carbon Compounds, E. L. Eliel, McGraw Hill (1962); "Tables of Resolving Agents" Wilen and Lochmuller, *J. Chromatography* 113, 283–302 (1975).] Additionally, the optically pure (+) isomer can be prepared from the racemic mixture by enzymatic biocatalytic resolution. See for example, U.S. Pat. Nos. 5,057,427 and 5,077,217, the disclosures of which are incorporated herein by reference.

The magnitude of a prophylactic or therapeutic dose of (+) doxazosin in the acute or chronic management of disease will vary with the severity of the condition to be treated, and the route of administration. The dose, and perhaps the dose frequency, will also vary according to the age, body weight, and response of the individual patient. In general, the total daily dose range, for (+) doxazosin, for the conditions described herein, is from about 0.1 mg to about 20 mg, in single or divided doses. Preferably, a daily dose range should be between about 0.1 mg to about 10 mg, in single or divided doses, while most preferably, a daily dose range should be between about 0.5 mg to about 5 mg, in single or divided doses. In managing the patient, the therapy should be initiated at a lower dose, perhaps about 0.5 mg to about 1 mg, and increased up to about 8 mg or higher depending on the patient's global response. It is further recommended that children, and patients over 65 years, and those with impaired renal, or hepatic function, initially receive low doses, and that they be titrated based on individual response(s) and blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response. The term "an amount sufficient to alleviate hypertension but insufficient to cause said adverse effects" is encompassed by the above-described dosage amounts and dose frequency schedule.

Any suitable route of administration may be employed for providing the patient with an effective dosage of (+) doxazosin. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise (+) doxazosin as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable nontoxic acids or bases including inorganic acids and bases and organic acids and bases. Since the compound of the present invention is basic, salts may be prepared from pharmaceutically acceptable nontoxic acids including inorganic and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic (mesylate), mucic, nitric, pamoic, pantothenic, phosphoric, succinic, sulfuric, tartaric, p-toluenesulfonic, and the like.

The compositions of the present invention include compositions such as suspensions, solutions, elixirs, aerosols, and solid dosage forms. Carriers such as starches, sugars, microcrystalline cellulose, diluents, granulating agents, lubricants, binders, disintegrating agents, and the like, are commonly used in the case of oral solid preparations (such as powders, capsules, and tablets), with the oral solid preparations being preferred over the oral liquid preparations. The most preferred oral solid preparation is tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos. 3,845,770; 3,916,899; 3,536,809; 3,598,123; and 4,008,719; the disclosures of which are hereby incorporated by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 0.5 mg to about 10 mg of the active ingredient. Most preferably, the tablet, cachet or capsule contains either one of three dosages, about 0.5 mg, about 2 mg, or about 8 mg of the active ingredient.

The invention is further defined by reference to the following examples describing in detail the preparation of the compositions of the present invention as well as their utility. It will be apparent to those skilled in the art that many modifications, both to materials and methods, may be practiced without departing from the purpose and interest of this invention.

EXAMPLE PROCEDURES $\alpha_1$-Adrenergic Binding Assay

Whole brains are obtained from male Wistar rats. After removal of the cerebellum, the brains are used to prepare the membrane fraction (see Greengrass, P. and Brenner, R. *Eur. J. Pharmacol.* 55: 323–326, 1979). The membrane preparation (10 mg) is incubated with 0.25 nM [$^3$H]-prazosin and varying concentrations of test substance for 30 minutes at 25° C. Membranes are filtered and washed 3 times and the filters counted to determine the amount of [$^3$H]-prazosin specifically bound. Non-specific binding is determined by incubation with 0.1 µM prazosin.

$\alpha_2$-Adrenergic Binding Assay

Brain cortices are removed from male Wistar rats and a membrane fraction is prepared (see Boyajian, C. L. and Leslie, F. M. *J. Pharmacol. Exp. Ther.* 241:1092–1098, 1987). The membrane preparation (10 mg) is incubated with 0.7 nM [$^3$H]-rauwolscine and varying concentrations of test substance for 30 minutes at 25° C. Membranes are filtered and washed 3 times and the filters counted to determine the amount of [$^3$H]-rauwolscine specifically bound. Non-specific binding is determined by incubation with 1 µM yohimbine.

Antihypertensive Efficacy in Spontaneously Hypertensive Rats

Male spontaneously hypertensive rats (300–350 g) are anesthetized, and polyethylene catheters are implanted in the abdominal aorta via a femoral artery and in the abdominal vena cava via a femoral vein. The arterial catheters are connected to pressure transducers by means of an intraflow device, flushing the catheters with 3 mL/hr. Mean arterial pressures are derived electronically from the blood pressure wave. Mean pretreatment values of mean arterial pressure are in the range of 160–220 mm Hg. Doses of racemic doxazosin, (+) doxazosin and (−) doxazosin, or of the solvent vehicle, are injected into the venous catheter. Responses in mean arterial pressure to the respective drug or solvent are registered and the relative potencies of the test compounds are calculated.

Orthostatic Hypotension and Reflex Tachycardia in Dogs

Groups of dogs are tested with suitable doses of racemic doxazosin, (−) doxazosin, and (+) doxazosin and the effects on blood pressure (orthostatic hypotension) and heart rate (reflex tachycardia) are monitored and recorded at predetermined time intervals. Conscious normotensive dogs with surgically implanted arterial catheters are used to study the effects of the drugs on orthostatic hypotension and heart rate. The animals may also be equipped with cutaneous electrodes connected to suitable equipment for recording electrocardiograms. The tip of the indwelling catheter is positioned at the junction between the aorta and the left carotid artery. Blood pressure is measured by means of a pressure transducer and heart rate is computed from the systolic peaks in blood pressure or from the R-waves of the EKG. Doses of the test compounds are given orally or parenterally and the effects on the cardiovascular parameters are initially recorded with the animals in normal standing position. The animals are then held by their front paws and lifted into an upright position, standing on their hind paws. Drugs causing orthostatic hypotension will cause a sudden fall in recorded arterial blood pressure, sometimes accompanied by a reflex tachycardia.

EXAMPLE 1

ORAL FORMULATION

Capsules:

| Formula | Quantity per capsule in mg | | |
|---|---|---|---|
| | A | B | C |
| (+) Doxazosin | 0.5 | 2.0 | 8.0 |
| Lactose | 84 | 82.5 | 76.5 |
| Cornstarch | 15 | 15 | 15 |
| Magnesium Stearate | 0.5 | 0.5 | 0.5 |
| Compression Weight | 100.0 | 100.0 | 100.0 |

The active ingredient, (+) doxazosin, is sieved and blended with the excipients. The mixture is filled into suitably sized two-piece hard gelatin capsules using suitable machinery. Other doses may be prepared by altering the fill weight and if necessary, changing the capsule size to suit.

EXAMPLE 2

ORAL FORMULATION

Tablets:

| Formula | Quantity per tablet in mg | | |
|---|---|---|---|
| | A | B | C |
| (+) Doxazosin | 0.5 | 2.0 | 8.0 |
| Lactose | 72.25 | 70.75 | 64.75 |
| Cornstarch | 3.0 | 3.0 | 3.0 |
| Water (per thousand Tablets)* | 30.0 mL | 30.0 mL | 30.0 mL |
| Cornstarch | 18.75 | 18.75 | 18.75 |
| Magnesium Stearate | 0.50 | 0.50 | 0.50 |
| Compression Weight | 125.0 | 125.0 | 125.0 |

*The water evaporates during manufacture

The active ingredient is blended with the lactose until a uniform blend is formed. The smaller quantity of cornstarch is blended with the water to form the resulting cornstarch paste. This is then mixed with the uniform blend until a uniform wet mass is formed and the remaining cornstarch is added and mixed until uniform granules are obtained. The granules are screened through a suitable milling machine using a ¼" stainless steel screen. The milled granules are dried in a suitable drying oven and milled through a suitable milling machine again. The magnesium stearate is then blended and the resulting mixture is compressed into tablets of desired shape, thickness, hardness and disintegration.

What is claimed is:

1. A method for treating hypertension in a human while avoiding the concomitant liability of adverse effects associated with racemic doxazosin, which comprises administering to a human, in need of antihypertensive therapy, an amount of (+) doxazosin, or a pharmaceutically acceptable salt thereof, substantially free of its (−) stereoisomer, said amount being sufficient to alleviate said hypertension but insufficient to cause said adverse effects.

2. The method of claim 1 wherein (+) doxazosin is administered by intravenous infusion, transdermal delivery, or orally as a tablet or a capsule.

3. The method of claim 2 wherein the amount of (+) doxazosin or a pharmaceutically acceptable salt thereof administered is from about 0.1 mg to about 20 mg per day.

4. The method of claim 3 wherein the amount administered is from about 0.5 mg to about 8 mg per day.

5. The method of claim 4 wherein the amount administered is from about 0.5 mg to about 2 mg per day.

6. The method of claim 1 wherein the amount of (+) doxazosin or a pharmaceutically acceptable salt thereof is greater than approximately 90% by weight of the total weight of doxazosin.

7. The method of claim 1 wherein the amount of said (+) doxazosin or a pharmaceutically acceptable salt thereof, substantially free of its (−) stereoisomer, is administered together with a pharmaceutically acceptable carrier.

8. The method according to claim 1, wherein (+) doxazosin is administered as a salt selected from the group consisting of hydrochloride and methane sulfonate.

* * * * *